United States Patent [19]

Lagnemo et al.

[11] Patent Number: 5,415,668
[45] Date of Patent: May 16, 1995

[54] DIACYLATED DIPERCARBOXYLIC ACID AS BLEACHING AGENT

[75] Inventors: Hans Lagnemo, Göteborg; Annbritt Forsström, Kungälv, both of Sweden

[73] Assignee: Eka Nobel AB, Bohus, Sweden

[21] Appl. No.: 946,343

[22] PCT Filed: Apr. 24, 1991

[86] PCT No.: PCT/SE91/00291
§ 371 Date: Nov. 6, 1992
§ 102(e) Date: Nov. 6, 1992

[87] PCT Pub. No.: WO91/17143
PCT Pub. Date: Nov. 14, 1991

[30] Foreign Application Priority Data

May 9, 1990 [SE] Sweden .................. 9001676

[51] Int. Cl.$^6$ .................. C11D 3/39; C11D 3/395; D06L 3/02
[52] U.S. Cl. .................. 8/111; 252/94; 252/95; 252/8.6; 252/8.7; 252/8.75; 252/8.8; 252/8.9; 252/186.42; 568/566
[58] Field of Search .................. 8/111; 252/94, 95, 8.6, 252/8.7, 8.75, 8.8, 8.9, 186.42; 586/566

[56] References Cited

U.S. PATENT DOCUMENTS

| | | |
|---|---|---|
| 3,287,338 | 11/1966 | Guillet . |
| 3,316,228 | 4/1967 | Guillet et al. . |
| 3,337,602 | 8/1967 | Guillet et al. . |
| 3,476,813 | 11/1969 | Guillet . |
| 3,652,631 | 3/1972 | Stevens et al. .................. 8/111 |
| 3,850,891 | 11/1974 | Crawford . |
| 4,756,845 | 7/1988 | Sugawara et al. .................. 252/95 |
| 4,824,591 | 4/1989 | Dyroff et al. . |

FOREIGN PATENT DOCUMENTS

| | | |
|---|---|---|
| 725694 | 1/1966 | Canada . |
| 0283252 | 9/1988 | European Pat. Off. . |
| 3227451 | 10/1991 | Japan . |

OTHER PUBLICATIONS

Kirk–Othmer Encyclopedia of Chemical Technology, 3rd Edition, vol. 3, (1978), pp. 944–945.
Chemical Abstracts #CA70(25):114529e, 1967 no month available.

(List continued on next page.)

Primary Examiner—Prince Willis, Jr.
Assistant Examiner—Alan D. Diamond
Attorney, Agent, or Firm—Burns, Doane, Swecker & Mathis

[57] ABSTRACT

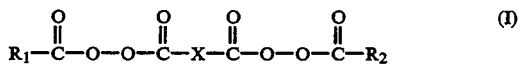

The invention concerns diacylated dipercarboxylic acids according to general formula (I), in which $R_1$ and $R_2$ are hydrocarbon groups having from 1 to 15 carbon atoms, and X is electron attracting by being an optionally substituted phenyl group, an optionally substituted heterocycle in which the hetero atom is positioned so that from 2 to 4 carbon atoms are present between the hetero atom and each one of the carbonyl carbons of the diperacid, or by comprising at least one electron attracting functional group positioned so that a carbon chain having from 2 to 4 carbon atoms is present between said electron attracting group and each one of the carbonyl carbons of the diperacid, wherein the electron attracting group contains oxygen, sulfur, nitrogen, phosphorus, halogen, optionally substituted phenyl, or at least two conjugated double bonds, $R_1$ and $R_2$ are hydrocarbon groups having from 1 to 15 carbon atoms, except compounds in which X consists of a phenyl group having the carbonyl carbons in 1,4 position and both of $R_1$ and $R_2$ are acetyl or both of $R_1$ and $R_2$ are nonyl. The invention also concerns a method of their preparation, a composition useful for bleaching and a method of bleaching.

9 Claims, No Drawings

OTHER PUBLICATIONS

Chemical Abstracts #CA69(1):2638n, 1968 no month available.

Chemical Abstracts #CA76(7):33579t, 1971 no month available.

Chemical Abstracts #CA97(16):128106j, 1982 no month available.

L. Heslinga et al, "Diperoxycarboxylic Anhydrides and Their Urea Adducts as Peroxy Acid Precursors", 85 (1966) Recueil, pp. 75–85, no month available.

Organic Peroxides, vol. 1, Fels Research Institute and Department of Chemistry, Temple University, Wiley-Interscience, pp. 65–67, 388–389 and 427–430, no month available.

Chem. Abstract, vol. 110 No. 7, Feb. 13, 1989, V. S. Dutka et al, "Induced decomposition of diacyl peroxides", see p. 619, Abstract 56930k.

Chemical Abstracts, vol. 79, No. 25, Dec. 24, 1973, Galibei et al, "Peroxide derivatives of dibasic aliphatic acids with diacyl and perester groups", p. 279, Abstract 145931.

DIACYLATED DIPERCARBOXYLIC ACID AS BLEACHING AGENT

The present invention concerns diacylated dipercarboxylic acids comprising an electron attracting functional group, a method of their preparation, a composition useful for bleaching and a method of bleaching.

At washing, of for example textiles, it is often desirable to add a bleaching agent, either separately or together with the detergent. Frequently hydrogen peroxide generating agents are used, generally perborates, which in alkaline environment generate hydrogen peroxide. The hydrogen peroxide decomposes into $H^+$ and $HO_2^-$, which has a bleaching effect at temperatures exceeding about 60° C. However, for achieving optimal effect a temperature at about 85° C. is necessary, which results in rather high energy consumption at washing.

Bleaching at lower temperatures can be achieved with percarboxylic acids which, however, are too unstable to be stored very long time. Attempts to stabilize the peracids, for example with the magnesium salt of monoperoxy phtalic acid or by phlegmatizing diperoxy dodecanoic acid in sodium sulfate, have not resulted in products good enough for commercial use. U.S. Pat. No. 4,824,591 disclose a peracid including a sulfonic group, which peracid is said to be more stable than previously known peracids. However, the reason for the improved stability is unclear. The use of percarboxylic acids at washing also involves the disadvantage of getting such a high initial concentration that the bleaching do not become uniform, resulting in stains. On the other hand, the concentration of the peracid falls quickly due to decomposition, resulting in no bleaching effect at all at the end of the washing cycle.

To avoid stability problems and to obtain a more constant concentration of percarboxylic acid in the washing water during the washing cycle, bleaching activators, such as TAED (tetra acetyl ethylenediamine) or TAGU (tetraacetyl glucolurile), are frequently used. In contact with hydrogen peroxide such an activator generates 1 mol percarboxylic acid per mol hydrogen peroxide. In order to obtain enough percarboxylic acids, rather lage amounts, of the activator as well as of the hydrogen peroxide, are thereby required.

Accordingly, there is a need for a bleaching agent which is stable during storage, gives a satisfying yield of percarboxylic acids in aqueous solutions and can be used without or with less supply of hydrogen peroxide than bleaching agents presently available. The agent should have capability to generate percarboxylic acids with a suitable rate to achieve a constant concentration during a whole washing cycle, and be compatible with other components in a detergent. Finally, it is desirable that it is harmless and inexpensive. Such a bleaching agent has now been found possible to provide through compounds with the general formula:

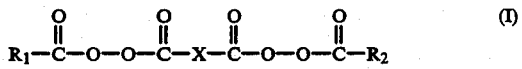

in which $R_1$ and $R_2$ are hydrocarbon groups and X is an electron attracting group.

The invention is based on the finding that an electron attracting group in the center of the molecule has an inductive effect on the closest carbonyl carbons, resulting in a non-uniform electron distribution which stabilizes the molecule against homolytic cleavage of the O—O bonds. In many per-compounds this cleavage can occur rapidly and involve explosions, and the free radicals thereby formed have almost no bleaching effect in practice. The stability against homolysis increases with the electron attracting force of X. Compared to corresponding diperacids, the stability is further increased by the acylation. In alkaline aqueous solutions the molecule undergoes hydrolysis via nucleophilic attack by hydroxyl ions against the carbonyl carbons, giving 2 percarboxylic acids, $R_1COOOH$ and $R_2COOOH$, or 1 dipercarboxylic acid, $X(COOOH)_2$. Which one of the reactions that dominates depends, among other things, on the X-group, but since both mono- and dipercarboxylic acids show a high bleaching effect it is not essential for the invention. If hydrogen peroxide is present, every 2 mols of the compound give 2 mols of percarboxylic acid and 1 mol of dipercarboxylic acid which is twice the yield compared to traditional bleaching activators.

Some diacylated dipercarboxylic acids according to formula (I) are known per se. CA patent 725694 (corresponds to U.S. Pat. Nos. 3,476,813 and 3,287,338) disclose such compounds as radical initiators for polymerization. This effect is achieved by homolytic decomposition at heating, which involves the cleavage of the O—O bonds, giving free radicals. In the preferred and according to the examples prepared compounds, the center groups X consist of alkyl groups, which are not electron attracting and thereby favour homolytic decomposition. At use as polymerization catalysts, they are solved in toluene, which indicates that aqueous solubility is not a desirable feature. The only specific compound mentioned not having an alkyl group in the center is diacetylated diperoxy terephtalic acid, but it has not been prepared and there is no indication that it would be soluble in water or that it would decompose and give peracids in an alkaline aqueous solution, which according to the present invention are features necessary for achieving a good bleaching effect. The patent also indicates the possibility that X may be phenyl, nitrophenyl, chlorophenyl, methylphenyl or methoxphenyl, but no specific compounds are mentioned. Even if bleaching is mentioned as a possible field of use, there is no guidance of its performance, and the preferred compounds would be unusable since they are not soluble in water and not stable enough against homolysis.

Chemical Abstracts 110:56930 mentions dinonylated diperoxy terephtalic acid, but there is no indication of its use.

It is possible to estimate the inductive effect of different groups by theoretical calculations. It has been found that the groups having suitable inductive effect comprise conjugated systems, such as phenyl groups, or contain electronegative atoms, such as oxygen, sulfur, nitrogen, phosphorus or halogens.

Compounds as claimed in claim 1 are new and comprise compounds according to formula (I), in which X is electron attracting by being an optionally substituted phenyl group, an optionally substituted heterocycle in which the hereto atom is positioned so that from 2 to 4 carbon atoms are present between the hetero atom and each one of the carbonyl carbons of the diperacid, or by comprising an electron attracting functional group positioned so that a carbon chain having from 2 to 4 carbon atoms is present between said electron attracting functional group and each one of the carbonyl carbons of the diperacid, wherein the electron attracting functional group contains oxygen, sulfur, nitrogen, phosphorus, halogen, optionally substituted phenyl, or at least two conjugated double bonds, $R_1$ and $R_2$ are hydrocarbon groups having from 1 to 15, preferably from 1 to 10 carbon atoms, except compounds known per se from the prior art, i.e. when X consists of a phenyl group having the carbonyl carbons in 1,4 position and both of $R_1$ and $R_2$ are acetyl or both of $R_1$ and $R_2$ are nonyl.

If X is a phenyl group the carbonyl carbons of the peracid are preferably in para position but they may also be in ortho or meta positions. If the phenyl group includes substituents they may also be in any positions. The substituents may for example include alkyl, alkenyl, oxygen containing groups such as alkoxy, hydroxy, nitro or carbonyl groups, nitrogen containing groups such as amine or nitrile groups, sulfur containing groups such as sulfo or thiol groups, or any other group compatible with the rest of the molecule and not rendering the compund insoluble in water. Substituents electron attracting as such and/or forming a conjugated system with the aromatic ring are particularly preferred, for example nitro, amino, sulfo, hydroxy, or carboxylic acid.

Electron attracting functional groups containing oxygen, sulfur, nitrogen or phosphorus may for example include thio, thiol, sulfoxide, sulfo, sulfino, sulfonyl, sulfonyloxo, sulfoneamide, ether, amine, quaternary amine, amineoxide, imine, nitrile, ketone, aidehyde, carboxylic acid, carboxylic acid halide, amide, ester, phosphate or optionally substituted heterocycles. Halogens may be present as substituents on alkyl, cycloalkyl or alkenyl groups. Among the halogens chlorine is preferred, but also bromine, iodine and fluorine can be used.

As previously mentioned, the stability against homolytic decomposition increases with the electron attracting force of X. However, this force must not be to strong since the molecule then may hydrolyze too rapidly. If x neither is an optionally substituted phenyl group nor an optionally substituted heterocycle, a carbon chain comprising at least 2 carbon atoms must be present between the electron attracting functional group and each one of the carbonyl carbons of the diperacid in order to limit the inductive effect and thus the tendency towards hydrolysis. However, there must not be more than 4 carbon atoms between the electron attracting functional group and the carbonyl carbons, since the inductive effect otherwise becomes to weak. The same reasoning is applicable if X is an optionally substituted heterocycle, in which case from 2 to 4 carbon atoms must be present between the hetero atom and the carbonyl carbons.

If X is electron attracting by comprising an electron attracting functional group positioned so that from 2 to 4 carbon atoms are present between that group and the carbonyl carbons of the diperacid, it may be characterized by the formula below:

$$B-Z-C \qquad (II)$$

in which B and C are alkyl or alkenyl having from 2 to 4 carbon atoms, or —. In the latter case the distances to the carbonyl carbons become 4 carbon atoms. Z comprises an electron attracting functional group as described above and may for instance be:

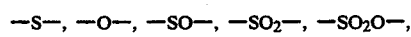

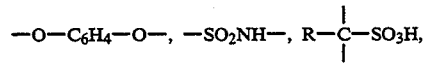

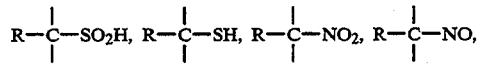

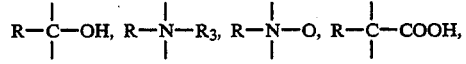

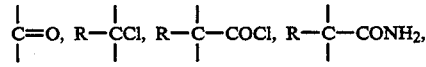

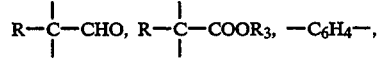

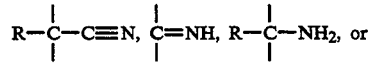

which R and $R_3$ ar hydrogen or a hydrocarbon group, preferably alkyl, most preferably a group having straight chains. Considering desirable aqueous solubility, the number of carbon atoms should not exceed 3, except for amine oxide and quaternary amine. An amine oxide may comprise an R-group having up to 12 carbon atoms, and a quaternary amine may comprise R and $R_3$ in which the sum of the number of carbon atoms is up to 12. Further examples of possible Z comprise phenyl groups substituted with for example alkyl, alkenyl, alkoxy, hydroxy, nitro, amine, sulfo or carboxylic acid groups. Z may also be a heterocycle, such as pyridine, piperidine, pyrrol, pyrrolidine, thiophene, furane or hydrofuran, including substituents or not.

Among the new compounds, those are preferred in which X consists of phenyl or a substituted phenyl group, or comprises an electron attracting group selected from sulfo, sulfonyl, thio, nitro, hydroxy, quaternary amine, amine oxide, carboxylic acid, ketone, aidehyde, ester or ether. Compounds in which x is phenyl, nitro phenyl, hydroxy phenyl, amino phenyl, sulfo phenyl, phenyl carboxylic acid, phenyl dicarboxylic acid, or comprises an electron attracting functional group selected from sulfonyl, amine oxide or quaternary amine, are particularly preferred.

The center-group X and the end-groups $R_1$ and $R_2$ should be selected so that the compound is soluble in water at the temperatures the compound is intended to be used at, in most cases from 20° to 100° C., especially from 35° to 65° C. The maximum length of the carbon chains of $R_1$ and $R_2$ depends on the X-group. A strong electron attracting group favours the aqueous solubility and enables longer endgroups. It has been found that peracids having from 2 to 3 and from 8 to 10 carbon atoms have the best bleaching effect, which peracids form when $R_1$ and $R_2$ includes from 1 to 2 or from 7 to 9 carbon atoms. Therefore, end-groups having up to 9 carbon atoms are the most interesting ones. Generally end-groups having 1 or 2 carbon atoms are preferred, since those compounds always are water-soluble if they comprise an X-group according to the invention. If the end-groups are longer they may comprise functional groups favouring the aqueous solubility, such as COOH and/or OH, quaternary amine or amineoxide. However, for reasons relating to economy, it is generally preferred that $R_1$ and $R_2$ are alkyl groups, especially groups having 1 or 2 carbon atoms.

The invention also concerns a method of preparing o the new diacylated dipercarboxylic acids according to the general formula (I). As a raw material a compound according to the formula below is selected:

$$A-X-A \quad (III)$$

in which A are COOOH, COOO⁻ or COY in which Y is a halogen, and X is electron attracting by being an optionally substituted phenyl group, an optionally substituted heterocycle in which the hetero atom is positioned so that from 2 to 4 carbon atoms are present between the hetero atom and each one of the two carbonyl carbons, or by comprising an electron attracting functional group positioned so that a carbon chain having from 2 to 4 carbon atoms is present between said functional group and each one of the two carbonyl carbons, wherein the electron attracting functional group contains oxygen, sulfur, nitrogen, phosphorus, halogen, optionally substituted phenyl, or at least two conjugated double bonds. The compound according to the formula A—X—A is brought to react with a carbonyl compound being a carboxylic acid anhydride or a carboxylic acid halide if A is COOOH or COOO⁻, a percarboxylic acid or its salt if A is COY. Said carbonyl compound comprise, in addition to the carbonyl group, also hydrocarbon groups $R_1$ and/or $R_2$ having from 1 to 15, preferably from 1 to 10 carbon atoms. Exceotion is made for the case when X consists of a phenyl group having the carbonyl carbons in 1,4 position and both $R_1$ and $R_2$ are acetyl or both $R_1$ and $R_2$ are nonyl. Thus, the preparation may be performed either by a reaction of a dipercarboxylic acid or its salt and a carboxylic acid anhydride or a carboxylic acid halide, preferably chloride, or by a reaction of a dicarboxylic acid halide, preferably chloride, with one or two different percarboxylic acids. The reaction is preferably performed in the presence of a phlegmatic agent. Phlegmatic agent refers to any inert substance compatible with the compounds according to the invention and the raw material for their preparation. Examples of suitable phlegmatic agents include zeolite such as 4A, 5A or 13X, molecular sieve such as 4A, 5A, 13X, or urea. Further examples include sulfate, hydrogen sulfate, phosphate, pyrophosphate, polyphosphate, nitrate, carbonate or silicate of alkali metals such as sodium or potassium, or of alkaline earth metals such as magnesium or calcium. Preferably the weight ratio phlegmatic agent/diacylated dipercarboxylic acid exceeds 1, most preferably it exceeds 2. The reaction may be performed in most inert organic solvents, such as ethylacetate, dichloromethane, diethylether, dimethylformamide or tetra hydrofurane, but also by adding an acid or an acid halide, in pure and liquid state or in a solvent, to a dry mixture of a peracid or its salt and a phlegmatic agent. It is also advantageous to add a sequestering agent, such as EDTA (ethylene diamine tetraacetic acid), NTA (nitrilo triacetic acid), dipicolinic acid or phosphonates, for example Dequest 2016® (sodium salt of 1-hydroxyethylene-(1,1-diphosphonic acid), Deqest 2040® or Dequest 2010®. It is also possible to add radical inhibitors such as phenol derivatives. It is preferred that the reactants are supplied in a substantially stoichiometric ratio. The reaction is suitably performed at a temperature from about 20° to about 80° C. and during a time from about 1 to about 10 hours. These parameters may vary depending on the compounds. To avoid handling of acid halides the reaction of a dipercarboxylic acid or its salt with carboxylic acid anhydride comprising $R_1$ and/or $R_2$, such as acetic acid anhydride or propionic acid anhydride, is often preferred. If not the anhydrides are easily available, suitably acid halogenides comprising $R_1$ and/or $R_2$ are used. The dipercarboxylic acids are prepared through the reaction of the corresponding dicarboxylic acid with peroxidizing agent, preferably hydrogen peroxide, in a strong acidic solvent, preferably methane-sulfonic acid or concentrated sulfuric acid. The reaction is suitably performed at a temperature not exceeding about 70° C. and during a time from about 1 to about 10 hours. Diperacids having low solubility in water generally precipitate at cooling to about 0°–10° C. In other cases, phase-supersaturation through the addition of salts, or other methods well known to the person skilled in the art, may be used. Preparation of dipercarboxylic acids is also described in D. Swern, "Organic Peroxides", John Wiley & sons inc., 1970, pp 388–389,427–430. Preparation of sulfonyl diperoxy acids is described in the previously mentioned U.S. Pat. No. 4,824,591. These acids may also be prepared in one step from thio diacids by peroxidizing with hydrogen peroxide in methane sulfonic acid or sulfuric acid, wherein the thio-group at the same time oxidizes to sulfonyl. If the isolation of the diperacids cause problems the other main method, i.e. the reaction of a diacid halide with a peracid or its salt, is preferred. Concerning preferred groups for X, $R_1$ and $R_2$, the description of the new compounds it referred to.

The invention also concerns a composition useful for bleaching in alkaline environment, comprising a phlegmatic agent and a water-soluble diacylated dipercarboxylic acid according to formula (I), in which X is electron attracting by being an optionally substituted phenyl group or an optionally substituted heterocycle in which the hetero atom is positioned so that from 2 to 4 carbon atoms are present between said hetero atom and each one of the two carbonyl carbons of the dipera-cid, or by comprising an electron attracting functional group positioned so that a carbon chain having from 2 to 4 carbon atoms is present between said electron attracting group and each one of the carbonyl carbons of the diperacid, wherein the electron attracting functional group contains oxygen, sulfur, nitrogen, phosphorus, halogen, optionally substituted phenyl or at least two conjugated double bonds, and $R_1$ and $R_2$ are hydrocarbon groups having from 1 to 15, preferably from 1–10 carbon atoms. Accordingly, the compounds known per se can be included in a composition according to the invention and can be prepared analogous with the new compounds. In fact, one of the particularly preferred compositions contains diacetylated diperoxy terephtalic acid. Concerning other preferred diacylated dipercarboxylic acids in the composition, the description of the new compounds is referred to.

Even if the diacylated dipercarboxylic acid according to the invention are proportionally stable, they should be mixed with a phlegmatic agent as a too high concentration of active oxygen may cause decomposition. The phlegmatic agent should be inert and compatible with the diacylated dipercarboxylic acid and with the other components present in the composition. Preferably it is also compatible with other components in a detergent. Examples of suitable phlegmatic agents include those mentioned in the description of the method of preparing the compounds according to the invention. Advantageously substances having other functions in a detergent, such as builders, fillers or substances active at washing can be used as a phlegmatic agent. The weight ratio phlegmatic agent/diacylated dipercarboxylic acid is preferably exceeding 1, most preferably exceeding 2. There is no critical upper limit, which limit is set by the lowest accepted concentration of diacylated dipercarboxylic acid in the composition, which concentration suitably is from about 0.5 to about 50% by weight, preferably from about 2 to about 20% by weight. Thus, the composition may contain up to about 99.5% by weight of phlegmatic agents. The values above are approximate due to the fact that different comoounds have different molecular weights and the essential feature is the amount of active oxygen. In the composition, the diacylated diperacids suitably contribute with from 0.1 to 10, preferably from 0.2 to 2 grams active oxygen per 100 grams of the composition.

In order to stabilize against decomposition catalyzed by metal cations, such as $Cu^{2+}$, $Mn^{2+}$ or $Fe^{3+}$, the composition may also may contain small amounts of sequestering agents, such as EDTA, NTA, dipicolinic acid, or phosphonates, for example Dequest 2010®, Dequest 2016® or Dequest 2040®, preferably in amounts from 0.1 to 1% by weight, and optionally in combination with magnesium silicate. Also radical inhibitors may be present, preferably in amounts from 0.1 to 0.5% by weight. A great number of radical inhibitors are useful, for example phenol derivatives such as hydrokinone, phenols having from 1 to 3 substituents such as alkyl, alkoxy, ester groups or oxygen groups, polynuclear phenols substituted as above, or blocked amines.

The bleaching agent works in alkaline aqueous solutions without hydrogen peroxide, but the bleaching effect is further increased if hydrogen peroxide is present. Therefore, the composition preferably contains a hydrogen peroxide generating agent, such as alkali metal salts of perborate, percarbonate, perphosphate or percarbamide. Preferably mono- or tetrahydrate of sodium perborate is used. Maximal effect is obtained when the molar ratio hydrogen peroxide/diacylated dipercarboxylic acid exceeds 2, especially when it exceeds 3. For economic reasons a molar ratio not exceeding 10 is generally preferred since usually no further improved effect is obtained at a higher ratio.

Compositions according to the invention are useful for all kinds of bleaching in alkaline environment, in which bleaching means oxidative decomposition of chromophoric systems, which regarding peracids probably is due to the oxidation of conjugated double bonds. The composition is specifically advantageous at bleaching in combination with cleaning, especially at washing of textiles, in which case a good bleaching effect is obtained at such low temperatures as 20° C. Thereby it may be in the form of a complete detergent of in the form of a bleaching agent to be added separately at washing. The composition suitably contains a detergent-builder, especially if it is a complete detergent, but also a separate bleaching agent may contain a builder. It is specifically advantageous if a builder and a phlegmatic agent is one and the same substance, for example zeolite, preferably zeolite 4A, 5A, or 13X. As optionally complementing or alternative builder a great number of other substances well known to the person skilled in the art may be used, such as phosphates or polycarboxylates.

A separate bleaching agent is preferably in the form of a powder and suitably contains from 2 to 50, preferably from 5 to 20% by weight of diacylated dipercarboxylic acids and a phlegmatic agent, for example zeolite and/or sodium sulfate, suitably from 4 to 98, preferably from 40 to 75% by weight. Furthermore, it may for example contain from 0 to 30, preferably from 10 to 20% by weight of perborate, from 0.1 to 1% by weight of seqfuestering agents, from 0.1 to 0.5% by weight of radical inhibitors. They may be prepared by dry mixing, agglomerating or spray drying of a slurry or a solution of the components. If the preparation includes spray drying the per-compounds should be added afterwards, since they may decompose at high temperatures. Also a liquid bleaching agent may be provided, wherein it consists of a solution containing a diacylated dipercarboxylic acid being free from water and alkaline substances.

Complete detergents are suitably in the form of a powder and may be prepared by conventional methods, such as dry mixing, agglomeration or spray drying of a slurry or a solution of the components. As in the case above, the per- compounds should not be supplied until after an optional spray drying. Suitably they contain from 0.5 to 15% by weight, preferably from 1 to 10% by weight of diacylated dipercarboxylic acids.

Suitably at least one phlegmatic agent and at least one builder are included. Preferably zoolite, most preferably zeolite 4A, 5A or 13X is used for both the purposes, and is then suitably present in an amount from 10 to 45% by weight, preferably in combination with from 3 to 5 % by weight of polycarboxylates. Also phosphates or other sequestering agents, such as EDTA, may be used in combination with or as an alternative to zeolites. If zeolites are not present, the composition should contain another phlegmatic agent.

The detergent should also contain one or more alkali generating agents. If phosphates are used as builders they also function as alkali generating agents. Otherwise, for example carbonates or silicates of alkali metals, preferably sodium and/or potassium, may be included, preferably in an amount from 5 to 35% by weight.

A complete detergent also contains substances active at washing in the form of surfactants, preferably anionic and/or nonionic and/or soaps. The anionic surfactants are preferably present in an amount form 5 to 20% by weight and may for example comprise linear alkylbenzene sulfonate, secondary alkansulfonate, alcoholethoxysulfate or alphaolefine sulfonate. The nonionic surfactants are suitably present in an amount from 2 to 11% by weight and may for example comprise alkoxylated compounds such as fatty alcohols, alkylphenols and alkylamines. The soaps are suitably present in an amount from 0.1 to 4% by weight and may for example comprise sodium or potassium salts of tallow. Also cationic surfactants such as quaternary ammonium compounds or imide azolinium salts, as well as amphoteric surfactants might be used.

However not necessary, it is preferred that the detergent composition also contains a hydrogen peroxide generating substance, preferably perborate, suitably in an amount from 0 to 25, preferably from 3 to 10% by weight. In addition, the detergent may contain known components such as water glass, carboxy methyl cellulose, enzymes, fillers such as sodium sulfate, foam regulators, perfumes, coloring agents and optical brighteners.

A complete detergent composition according to the invention may for example include the following main components in % by weight up to 100%:

| | |
|---|---|
| diacylated dipercarboxylic acids | 1–10 |
| perborate | 5–15 |
| anionic surfactants | 5–20 |
| nonionic surfactants | 2–11 |
| soaps | 0,1–4 |
| sequestering agents | 0,1–1 |
| fillers | 16–50 |
| zeolites | 10–45 |
| polycarboxylates | 3–5 |
| sodium carbonate | 5–15 |

It is possible to further reduce the amount of fillers for obtaining a more concentrated detergent, in which the ratio between the other components should be substantially unchanged. A detergent as above, but without a bleaching agent, can advantageously be used in combination with a separate bleaching agent according to the invention as described.

A composition according to the invention may also constitute a semi-product for the preparation of a bleaching agent or a complete detergent according to the invention. Generally it is suitable if a semi-product is as concentrated as possible. However, for reasons of stability it should not contain more than 10% by weight of active oxygen. A suitable semi-product may for example contain from 20 to 50% by weight of diacylated dipercarboxylic acids and from 45 to 80% by weight of a phlegmatic agent. Further, from 0.1 to 1% by weight of sequestering agents and/or from 0.1 to 0.5% by weight of radical inhibitors may be included.

Finally, the invention concerns a method of bleaching, i.e. oxidative decomposition of chromophoric systems, in alkaline environment, by bringing the material to be bleached in contact with an alkaline aqueous solution containing a diacylated dipercarboxylic acid as described in connection with the composition according to the invention. Concerning preferred compounds to be used, the description of the new compunds and the composition according to the invention is referred to.

The content of diacylated dicarboxylic acid in the aqueous solution is suitably as high as it contributes with from 2 to 200 mg, preferably from 10 to 60 mg active oxygen per liter. This generally means that the amount of diacylated dipercarboxylic acid is from about 0.04 to about 1.3, preferably from about 0.08 to about 0.8 grams/liter. The pH-value of the aqueous solution should be from about 9 to about 12, preferably from about 9.5 to about 10.5, for the hydrolysis. and the formation of peracids to occur. The temperature must be high enough for enabling the diacylated dipercarboxylic acids used to dissolve in the water. Generally it is preferred that the temperature of the aqueous solution is from 20° to 100° C., preferably from 35° to 65° C. A good result of the bleaching is achieved without hydrogen peroxide, but it is further improved if the aqueous solution also contains hydrogen peroxide and/or a hydrogen peroxide generating agent in an amount so that the molar ratio hydrogen peroxide/diacylated dipercarboxylic acid is exceeding 2, preferably exceeding 3. In combination with cleaning or washing it is also preferred that the aqueous solution contains one or several surfactants.

The method of bleaching is preferably performed by dosing a composition according to the invention in water so that an suitable amount of active oxygen from the diacylated dicarboxylic acids is obtained. If a separate bleaching agent is used, an alkaline agent must also be supplied, preferably to a pH-value of the aqueous solution from about 9 to about 12, which preferably is achieved by the addition of a detergent containing an alkali generating agent but without bleaching agents. If a complete detergent according to the invention is used, it suitably contains an alkali generating agent.

The invention is now to be described through a number of non-restricting examples. All determinations of the amount of active oxygen have been performed by iodometric titrations after oxidation of possibly remaining hydrogen peroxide by potassium permanganate. If not otherwise stated, all percentages are in % by weight.

EXAMPLE 1a

Preparation of 3,3-sulfonyl dipropionic acid: 100 g (0.56 mol) 3,3-thiodipropionic acid and 540 ml ice-cold acetic acid were mixed in a 1000 ml reaction flask and temperated to 25° C. 72.5 ml (0.74 mol) 35% hydrogen peroxide was added by drops during 15 minutes under simultaneous agitation and cooling, keeping the temperature at about 30° C. After another 10 minutes agitation the mixture was cooled to 25° C. and poured into a 2000 ml beaker, except 100 ml which was left in the reaction flask, to which flask another 72.5 ml 35% hydrogen peroxide was added under agitation. The content of the reaction flask was then heated under agitation to 50° C. and the content in the beaker was added by drops during 15 minutes, whereupon the beaker was rinsed with 25 ml ice-cold acetic acid which was poured into the reaction flask. After 60 minutes of reaction the mixture was cooled to 25° C. and the excess of hydrogen peroxide was destroyed by the addition of 125 ml 5% $Na_2SO_3$ solution. The solid precipitation was filtered off and washed with 4×100 ml water and finally dried in a desiccator until constant weight.

EXAMPLE 1b cPreparation of 3,3-sulfonyl diperoxy dipropionic acid: 20 g (0.095 mol) 3,3-sulfonyl dipropionic acid prepared according to example 1a was dissolved in 120 ml 98% methane-sulfonic acid under agitation for 15 minutes at 35°–40° C., whereupon the solution was cooled to 15° C. 27.5 g (0.57 mol) 70% hydrogen peroxide was added by drops during 20 minutes and simultaneous cooling, keeping the temperature below about 25° C. After 2 hours reaction at 40° C the mixture was cooled in an ice-bath whereupon the solid particles were filtered off, washed in 4×30 ml ice-water and dried in a desiccator until constant weight.

EXAMPLE 1c

Preparation of diacetylated 3,3-sulfonyl diperoxy dipropionic acid: 2.00 g (8.26 mols) 3,3-sulfonyl diperoxy dipropionic acid prepared according to example 1b was mixed with 7.23 g (120.4 m mols) urea in a mortar to a homogeneous powder. 1.69 g (16,52 m mols) acetic acid anhydride was added by drops during 10 minutes and simultaneous agitation, wherein crystals formed. The crystals were heated to 40° C. during 1 hour and was then dried over KOH in a desiccator until constant weight.

EXAMPLE 1d

Preparation of diacetylated 3,3-sulfonyl diperoxy dipropionic acid: The procedure according to example 1c was repeated, with the exception that the urea was replaced by 7.54 g zeolite 4A.

EXAMPLE 1e

Preparation of diacetylated 3,3-sulfonyl diperoxy dipropionic acid: 2.00 g 3,3-sulfonyl diperoxy dipropionic acid prepared according to example 1b was dissolved in 30 ml dichloro methane at 25° C., whereupon 1.69 g (16.52 m mols) acetic acid anhydride was added by drops during 10 minutes and simultaneous agitation. Then 7.54 g zeolite 4A was added, the temperature was increased to 40° C. and the mixture was allowed to stand for an hour under a reflux cooler. Finally the dichloro methane was evaporated and the solid particles were collected and dried over KOH until constant weight.

EXAMPLE 1f

Preparation of diacetylated 3,3-sulfonyl diperoxy dipropionic acid: The procedure according to example 1e was repeated with the exception that the dichloro methane was replaced by diethyl ether.

EXAMPLE 1g

Preparation of diacetylated 3,3-sulfonyl diperoxy dipropionic acid: The procedure according to example 1e with the exception that the dichloro methane was replaced by dimethyl formamide.

EXAMPLE 1h mPreparation of diacetylated 3,3-sulfonyl diperoxy dipropionic acid: The procedure according to example 1e was repeated with the exception that the dichloro methane was replaced by ethyl acetate and that a stabilizing agent in the form of 0.01 g hydrokinon and 0.01 g Dequest 2016 ® were added to the solution.

EXAMPLE 2

Preparation of dipropylated 3,3-sulfonyl diperoxy dipropionic acid: 2.00 g (8,26 m mols) 3,3-sulfonyl diperoxy dipropionic acid prepared according to example 1b and 8.28 g (137.9 m mols) urea were mixed in a mortar to a homogeneous powder. 2.15 g (16.52 m mols) propionic acid anhydride was added by drops during 10 minutes and simultaneous agitation, wherein crystals formed. The crystals were heated to 40° C. during 1 hour and dried over KOH in a desiccator until constant weight.

EXAMPLE 3a

Preparation of diperoxy terephtalic acid: 10 g (51.5 m mols) terephtalic acid dimethylester was dissolved in 100 g methane-sulfonic acid under agitation at room temperature. The solution was cooled to 15° C., whereupon 15 g (0.309 mol) 70% hydrogen peroxide was added by drops under agitation. The temperature was increased and kept at 50° C. for 2 hours. The product was cooled to 0°–10° C., whereupon the solid particles were filtered off, washed with 4×30 ml ice-water and dried in a desiccator until constant weight.

EXAMPLE 3b

Preparation of diacetylated diperoxy terephtalic acid: 2.50 g (12.9 m mols) diperoxy terephtalic acid prepared according to example 3a was dissolved in 40 ml ethylacetate at room temperature, whereupon 0.1 g Dequest 2016 ® and 0.01 g hydrokinon were added. 2.63 g (25.8 m tools) acetic acid anhydride was added by drops at room temperature during 10 minutes, whereupon 9.40 g zeolite 4A was added and the temperature was increased. After 2 hours at 40° C. under a reflux cooler the ethyl acetate was evaporated at 40° C. under vacuum and the product was dried over KOH until constant weight.

EXAMPLE 3c

Preparation of diacetylated diperoxy terephtalic acid: 2.50 g (12.9 m mols) diperoxy terephtalic acid prepared according to example 3a, 9.40 g urea, 0.01 g Dequest 2016 ® and 0.01 g hydrokinon were mixed in a mortar to a homogeneous powder. 2.63 g (25.8 m mols) acetic acid anhydride was added by drops at room temperature and simultaneous agitation, wherein crystals formed. After 2 hours at 40° C. the product was dried over KOH until constant weight.

EXAMPLE 3d

Preparation of diacetylated diperoxy terephtalic acid: 5.00 g (25.2 m mols) diperoxy terephtalic acid prepared according to example 3a was dissolved in 300 ml tetra hydrofurane, whereupon 0.1 g Dequest 2016 ® and 0.01 g hydrokinon were added. 8.00 g (78.4 m mols) acetic acid anhydride was added by drops during 30 minutes, whereupon the temperature was increased and kept at 40° C. during 2 hours until the solution had become faintly yellow. The solution, which had become faintly yellow was cooled to below 10° C. and the tetra hydrofurane was evaporated in a film evaporator. The crystals were dried over KOH until constant weight.

EXAMPLE 4a

Preparation of 5-amino diperoxy isophtalic acid methylsulfonate: 2.00 g (0.011 mol) 5-amino isophtalic acid was dissolved in 30 g 98% methane-sulfonic acid during 15 minutes at 35° C., whereupon the solution was cooled to 15° C. and 2.70 g (0.068 mol) 85% hydrogen peroxide was added by drops during 10 minutes, the temperature not exceeding 25° C. The reaction mixture was allowed to stand for 2 hours at 25° C., whereupon 800 ml ethyl acetate (5°–10° C.) was added and the mixture was allowed to stand under vigorous agitation for 1 hour. The particles formed were filtered off and washed with 2×25 ml ethyl acetate. Titration on active oxygen showed a yield of 74.4%.

EXAMPLE 4b

Preparation of diacetylated 5-amino diperoxy isophtalic acid methylsulfonate: 2.50 g (0.008 mol) of the product from example 4a, 9.40 g dried zeolite 4A and 0.01 g dequest 2016 ® were mixed in a mortar to a homogeneous powder, whereupon 1.63 g (0.016 mol) acetic acid anhydride was added by drops under agitation. The powder-mixture was allowed to stand for 1 hour at 40° C. and was the dried over KOH until constant weight.

EXAMPLE 4c

Preparation of diacetylated 5-amino diperoxy isophtalic acid methylsulfonate: 2.50 g (0.008 mol) of the product from example 4a was dissolved in 40 ml ethyl acetate at 20° C., whereupon 9.40 g zeolite 4A and 0.1 g Dequest 2016 ® -were added. 1.63 g (0.016 mol) acetic acid anhydride was added by drops at 20° C., whereupon the temperature was increased and the mixture was allowed to stand for 1 hour under a reflux cooler at 40° C. The ethyl acetate was evaporated and the remaining solid powder was dried until constant weight.

EXAMPLE 5a

Preparation of 5-nitro peroxy isophtalic acid: 2.63 g (0.011 mol) 5-nitro isophtalic acid methylester was dissolved in 30 ml methane-sulfonic acid during 1 hour at 35° C. The solution was cooled to 15° C. and 2.64 g (0.066 mol) 85% hydrogen peroxide was added by drops during 10 minutes, the temperature not exceeding 25° C. After 2 hours reaction at 30° C., 400 ml ethyl acetate (0°-10° C.) and 100 ml saturated $(NH_4)_2SO_4$ solution were added, whereupon the mixture was allowed to stand for 2 hours under vigorous agitation. The ethyl acetate phase was separated off, dried over $Na_2SO_4$ and the ethyl acetate was evaporated until a yellow-brown oil was obtained. 5-nitro diperoxy isophtalic acid crystallized at the addition of diethylether/-hexane, and the yield of active oxygen obtained was 75%.

EXAMPLE 5b

Preparation of diacetylated 5-nitro peroxy isophtalic acid: 2.50 g (0.010 mol) 5-nitro diperoxy isophtalic acid prepared according to example 5a, 9.40 g dried zeolite 4A and 0.01 g Dequest 2016 ® were mixed in a mortar to a homogeneous powder. 2.04 g (0.020 mol) acetic acid anhydride was added by drops under agitation. The powder-mixture was allowed to stand for 1 hour at 40° C. and was then dried over KOH until constant weight.

EXAMPLE 5c

Preparation of diacetylated 5-nitro peroxy isophtalic acid: 2.50 g (0.010 mol) 5-nitro diperoxy isophtalic acid prepared according to example 5a was dissolved in 40 ml tert. butyl-methyl ether at 20° C., whereupon 9.40 g dried zeolite 4A and 0.01 g Dequest 2016 ® were added. 2.04 g (0.020 mol) acetic acid anhydride was added by drops at 20° C., whereupon the temperature was increased and the mixture was allowed to stand 1 for hour under a reflux cooler at 40° C. The ethylacetate was evaporated and the remaining solid powder was dried over KOH until constant weight.

EXAMPLE 6a

Preparation of 5-sulfo diperoxy isophtalic acid: 4.00 g (0. 0149 mol) 5-sulfo isophtalic acid was dissolved in 11.00 g 98% sulfuric acid at 35° C. during 1 hour and was then cooled to 15° C. 3.58 g (0.895 mol) 85% hydrogen peroxide was added by drops, the temperature not exceeding 25° C. After 2 hours reaction at 35° C., 200 ml saturated $Na_2SO_4$ solution and a few grams of solid $Na_2SO_4$ were added. The solution was poured into cold tert.butylmethyl ether and was allowed to stand for 2 hours under agitation. The tert.butyl-methyl ether phase was separated and dried over $Na_2SO_4$, whereupon the solvent was evaporated and 5-sulfo diperoxy isophtalic acid precipitated as crystals. The yield of active oxygen was 80.6%.

EXAMPLE 6b

Preparation of diacetylated 5-sulfo diperoxy isophtalic acid: 2.50 g (0. 009 mol) 5-sulfo diperoxy isophtalic acid prepared according to example 6a, 9.40 g dried zeolite 4A and 0.01 g Dequest 2016 ® were mixed in a mortar to a homogeneous powder, whereupon 1.83 g (0. 018 mol) acetic acid anhydride was added by drops under agitation. The powder-mixture was allowed to stand for 1 hour at 40° C. and was then dried until constant weight.

EXAMPLE 6c

Preparation of diacetylated 5-sulfo diperoxy isophtalic acid: 2.50 (0.009 mol) 5-sulfo diperoxy isophtalic acid prepared according to example 6a was dissolved in 40 ml ethyl acetate at 20° C., whereupon 9.40 g dried zeolite 4A and 0.01 g Dequest 2016 ® were added. 1.83 g (0.018 mol) acetic acid anhydride was added by drops at 20° C., whereupon the temperature was increased and the mixture was allowed to stand for 1 hour at 40° C. under a reflux cooler. The ethyl acetate was evaporated and the remaining solid powder was dried over KOH until constant weight.

EXAMPLE 7a

Preparation of butyl imino dipropionic acid: 61.9 g (0.847 mol) butylamine was dissolved in 110 g ethanol and was heated to 70° C., whereupon 169 g (1.694 mol) ethyl acrylate was added by drops during 45 minutes. After 12 hours reaction at 70° C., the mixture was cooled to 20° C. and 74.56 g (1.864 mol) NaOH in the form of an aqueous solution was added, wherein the temperature rose to 50° C. The mixture was boiled for 5 hours at 82° C. under reflux and was then cooled to 20° C. The ethanol and the water was evaporated until a yellow-brown oil remained, whereupon the product was dissolved again in 100 g ethanol which was evaporated. The yield was determined to 92.6%.

EXAMPLE 7b

Preparation of butyl imino dipropionic acid oxide: 100 g butyl imino dipropionic acid (0.46 mol) from example 7a was dissolved in 100 g $H_2O$, whereupon 0.10 g EDTA was added and the temperature was increased to 50° C. After 30 minutes 3.2 g (0.475 mol) 50% hydrogen peroxide was added by drops during 20 minutes and the mixture reacted for 2 hours at 75° C. under a reflux cooler. Then the water was evaporated at 40° C. until a slightly yellow-brown oil formed.

EXAHPLE 7c

Preparation of butyl imino diperoxy propionic acid oxide: 5 g (0.021 mol) product from example 7b was dissolved in 10 ml 98% methane-sulfonic acid during 10 minutes at 35° C. and was then cooled to 15° C. 5.14 (0.128 mol) 85% hydrogen peroxide was added by drops, the temperature not exceeding 25° C. After 2 hours at 30° C., 400 ml ice-cold (0°-10° C.) ethyl acetate and 100 ml saturated $(NH_4)_2SO_4$ solution were added and the mixture was allowed to stand for another 2 hours under agitation. The ethyl acetate phase was separated and dried over $Na_2SO_4$, whereupon the ethyl acetate was evaporated at 30° C. until a slightly yellow, viscous oil formed. Titration on active oxygen showed a yield of 72%.

EXAMPLE 7d

Preparation of diacetylated butyl imino dipropionic acid: 2.50 g (0.009 mol) product from example 7c was dissolved in 40 ml ethyl acetate at 20° C., whereupon 9.40 g dried zeolite 4A and 0.01 g Dequest 2016 ® were added. 1.84 (0.018 mol) acetic acid anhydride awas added by drops at 20° C., whereupon the temperature was increased and the mixture was allowed to stand for 1 hour at 40° C. under a reflux cooler. The ethyl acetate was evaporated and the remaining solid powder was dried over KOH until constant weight.

EXAMPLE 8a

Preparation of 4,4-sulfonyl diperoxy benzoic acid: 2.00 g (0.006 mol) sulfonyl dimethyl benzoate and 6 ml 98% methane-sulfonic acid were mixed and heated to 60° C., whereupon 1.75 g (0.036 mol) 70% hydrogen peroxide was added by drops during 10 minutes. After 3 hours at 60° C. the slurry obtained was cooled and filtered. Finally it was washed with 3×20 ml phosphate-buffer pH 5 and was dried over $Na_2SO_4$ until constant weight. Titration on active oxygen showed a yield of 62%.

EXAMPLE 8b

Preparation of diacetylated 4,4-sulfonyl diperoxy benzoic acid: 2.50 g (0.007 mol) 4,4-sulfonyl diperoxy benzoic acid from example 8a, 9.40 g dried zeolite 4A and 0.01 g Dequest 2016 ® were mixed in a mortar to a homogeneous powder, whereupon 1.43 g (0.014 mol) acetic acid anhydride was added by drops under agitation. The powder-mixture was allowed to stand for 1 hour at 40° C. and was then dried over KOH until constant weight.

EXAMPLE 8c

Preparation of diacetylated 4,4-sulfonyl diperoxy benzoic acid: 2.50 g (0.007 mol) 4,4-sulfonyl diperoxy benzoic acid from example 8a was dissolved in 40 ml ethyl acetate at 20° C., whereupon 9.40 g dried zeolite 4A and 0.01 g Dequest 2016 ® were added. 1.43 g (0.014 mol) acetic acid anhydride was added by drops at 20° C., whereupon the temperature was increased land the mixture was allowed to stand for 1 hour at 40° C. under a reflux cooler. The ethyl acetate was evaporated and the remaining solid powder was dried over KOH until constant weight.

EXAMPLE 9a

Preparation of diperoxy trimellitic acid: 4.00 g (0.0221 mol) trimellitic acid anhydride was dissolved in 60 ml 98% methane-sulfonic acid and 20 ml 98% sulfuric acid during 1 hour at 40° C. and was then cooled to 15° C. 4.99 g (0.125 mol) 85% hydrogen peroxide was added by drops during 15 minutes. After 2 hours at 30° C. the mixture was cooled and gently poured into 800 ml ice-cold (0°–10° C.) ethyl acetate under agitation, whereupon 200 ml saturated $(NH_4)_2SO_4$ solution was added. After 2 hours vigorous agitation the ethyl acetate phase was separated and dried over $Na_2SO_4$. The ethyl acetate was evaporated until a viscous yellow-white oil remained. Diperoxy trimellitic acid crystallized in petroleum-ether/diethylether and was dried until constant weight. Titration on active oxygen showed a yield of 70.7%.

EXAMPLE 9b

Preparation of diacetylated diperoxy trimellitic acid: 2.50 g (0.011 mol) diperoxy trimellitic acid prepared according to example 9a, 9.40 g dried zeolite 4A and 0.01 g Dequest 2016 ® were mixed in a mortar to a homogeneous powder, whereupon 2.24 g (0.022 mol) acetic acid anhydride was added by drops under agitation. The powder-mixture was allowed to stand for 1 hour at 40° C. and was the dried over KOH until constant weight.

EXAMPLE 9c

Preparation of diacetylated diperoxy trimellitic acid: 2.50 g (0.011 mol) diperoxy trimellitic acid prepared according to example 9a was dissolved in 40 ml ethyl acetate at 20° C., whereupon 9.40 g dried zeolite 4A and 0.01 g Dequest 2016 ® were added. 2.24 g (0.022 mol) acetic acid anhydride was added by drops at 20° C., whereupon the temperature was increased and the mixture was allowed to stand for 1 hour at 40° C. under a reflux cooler. The ethyl acetate was evaporated and the remaining solid powder was dried over KOH until constant weight.

EXAMPLE 10a

Preparation of diperoxy pyromeltitic acid: 4.00 g (0.016 mol) pyromellitic acid was dissolved in 60 ml 98% methane-sulfonic acid and 30 ml sulfuric acid at 40° C. during 45 minutes and was then cooled to 15° C. 3.78 g (0.094 mol) 85% hydrogen peroxide was added by drops during 10 minutes. After 3 hours at 35° C., the mixture was cooled to 5° C. and poured into 800 ml ice-cold (0°–10° C.) ethyl acetate under agitation. 200 ml saturated $(NH_4)_2SO_4$ solution was added, and after 1 hour of vigorous agitation the ethyl acetate was separated and dried over $Na_2SO_4$. The ethyl acetate was evaporated until a white precipitation formed, which was washed with 3×20 ml saturated $(NH_4)_2SO_4$ solution and dried until constant weight. Titration on active oxygen showed a yield of 66.5%.

EXAMPLE 10b

Preparation of diacetylated diperoxy pyromellitic acid: 2.50 g (0.009 mol) diperoxy pyromellitic acid prepared according to example 10a, 9.40 g dried zeolite 4A and 0.01 g Dequest 2016 ® were mixed in a mortar to a homogeneous powder, whereupon 1.84 g (0. 018 mol) acetic acid anhydride was added by drops under agitation. The powder-mixture was allowed to stand for 1 hour at 40° C. and was then dried over KOH until constant weight.

EXAMPLE 10c

Preparation of diacetylated diperoxy pyromellitic acid: 2.50 g (0.009 mol) diperoxy pyromellitic acid prepared according to example 10a was dissolved in 40 ml ethyl acetate at 20° C., whereupon 9.40 g dried zeolite 4A and 0.01 g Dequest 2016 ® were added. 1.84 g (0.018 mol) acetic acid anhydride was added by drops at 20° C., whereupon the temperature was increased and the mixture was allowed to stand at 40° C. under a reflux cooler. The ethyl acetate was evaporated and the remaining solid powder was dried over KOH until constant weight.

EXAMPLE 11

Preparation of dihexanoyl-3,3-sulfonyl diperoxy propionic acid: 2.50 g (0.0101) 3,3-sulfonyl diperoxy dipropionic acid prepared according to example 1b was dissolved in 25 ml methylene chloride and cooled to 0° C., whereupon 3.65 grams (0.0206 mol) hexanoic acid chloride solved in 25 ml methylene chloride was added. The reaction mixture was cooled to 0° C. and 1.63 g (0.0206 mol) pyridine was added by drops during 10 minutes. After 45 minutes the temperature was increased to 20° C. After 1 hour, the solution was washed with 3×50 ml H₂O and the methylene chloride phase was dried over MgSO₄. After evaporation crystals formed, which were dried until constant weight.

EXAMPLE 12

Preparation of dinonanoyl-3,3-sulfonyl diperoxy propionic acid: 2.50 g (0.0101) 3,3-sulfonyl diperoxy dipropionic acid prepared according to example 1b was dissolved in 25 ml methylene chloride and cooled to 0° C., whereupon 3.65 grams (0. 0206 mol) nonanoic acid chloride solved in 25 ml methylene chloride was added. The reaction mixture was cooled to 0° C. and 1.63 g (0.0206 mol) pyridine was added by drops during 10 minutes. After 45 minutes the temperature was increased to 20° C. After 1 hour the solution was washed with 3×50 ml H₂O and the methylene chloride phase was dried over MgSO₄. After evaporation crystals formed, which were dried until constant weight.

EXAMPLE 13

0.5 g product prepared according to example 1b, containing 0.14 g diacetylated 3,3-sulfonyl diperoxy dipropionic acid, the balance substantially being zeolite 4A, was dissolved in 100 ml deionized water at 40° C. together with 0.149 g sodium perborate monohydrate and 1 g IEC standard detergent from Henkel (6.4% by weight of linear sodium alkyl benzenesulfonate, 2.3% by weight of sodium-soap, 35% by weight of sodium triphosphate, 6% by weight of sodium waterglass (ratio 3.3), 1.5% by weight of magnesium silicate, 1.0% by weight of carboxy methyl cellulose, 0.2% by weight of EDTA, 0.2% by weight of optical brightener (stilbene type), 16.8% by weight of sodium sulfate, 7.8 % by weight of water). A corresponding solution was prepared from 0.192 g TAED, 0.3 g sodium perborate monohydrate, 1 g IEC standard detergent and 100 ml deionized water at 40°. After 5, 10 and 15 minutes, samples of 10 ml were taken from each solution to determine the yield of active oxygen (A.O.). The table below shows the number of grams of active oxygen per gram of active substance.

| Active substance | Yield grams A.O./gram active substance | | |
|---|---|---|---|
| | 5 min | 10 min | 15 min |
| diacetylated 3,3-sulfonyl diperoxy dipropionic acid | 0,14 | 0,12 | 0,09 |
| TAED | 0,12 | 0,11 | 0,09 |

The experiment show that the compound according to the invention gives a slightly higher yield of active oxygen than obtained with the conventionally used TAED, in spite of the fact that the amount of hydrogen peroxide generating agent (perborate) is less.

EXAMPLE 14

Product prepared according to example 1h, i.e. diacetylated 3,3-sulfonyl diperoxy dipropionic acid mixed with zeolite 4A, was stored. The yield of active oxygen was determined after 10, 18, 30, 40, and 280 days storage at room temperature. The method of determinations used was the same as in example 13. The results appear from the table below:

| Storage time (days) | Yield grams A.O./gram active substance | | |
|---|---|---|---|
| | 5 min | 10 min | 15 min |
| 10 | 0,14 | 0,11 | 0,10 |
| 38 | 0,14 | 0,11 | 0,09 |
| 30 | 0,14 | 0,11 | 0,09 |
| 40 | 0,14 | 0,12 | 0,09 |
| 280 | 0,13 | 0,11 | 0,11 |

The experiment show that the content of active oxygen in the detergent solutions obtained is substantially unchanged after 280 day storage of the diacylated dipercarboxylic acids according to the invention.

EXAMPLE 15

0.44 g product prepared according to example 1h, i.e. 0.12 g diacetylated 3,3-sulfonyl diperoxy dipropionic acid (DADPSPA), the balance substantially being zeolite 4A, was dissolved in 1000 ml water together with 0.26 g sodium perborate monohydrate (PBM) and 5 g IEC standard detergent. Corresponding solutions were prepared from 0.597 g product prepared according to example 3c, i.e. 0.16 g diacetylated diperoxy terephtalic acid (DADPTA), 0.26 g (PBM), 5 g IEC, and from 0.12 g TAED, 0.26 g PBM and 4.2 g IEC. Further, solutions containing twice the amount of DADPSPA and DADPTA respectively but no perborate, were prepared (referred to as *2). The bleaching effect of the solutions were tested by washing pieces of cloth for 15 minutes at 40° and 60° C., the pieces of cloths being presoiled with tea (WFK 10G), coffee (WFK 10K) and red wine (EMPA 114). The brightness was determined prior to and after the washing with a reflectance meter at a wave-length of 457 nm, whereupon the differences were transformed to percent bleaching effect. The results appear from the table below.

| Bleaching agent | temp (°C.) | Bleaching effect (%) | | |
|---|---|---|---|---|
| | | Tea | Coffee | Red wine |
| DADSPA + PBM | 40 | 57 | 70 | 48 |
| DADSPA *2 | 40 | 63 | 74 | 53 |
| DADSPA *2 | 60 | 73 | 82 | 60 |
| DADPTA + PBM | 40 | 58 | 72 | 46 |
| DADPTA *2 | 40 | 58 | 68 | 47 |
| DADPTA + PBM | 60 | 76 | 82 | 58 |
| DADPTA *2 | 60 | 77 | 83 | 60 |
| TAED + PBM | 40 | 59 | 70 | 48 |

The experiments show that diacylated dipercarboxylic acids give a very good bleaching effect, in combination with hydrogen peroxide as well as without. Even at low washing temperatures the effect is good.

We claim:
1. A composition useful for bleaching in alkaline environment, comprising a phlegmatic agent and a water-soluble diacylated dipercarboxylic acid according to the formula:

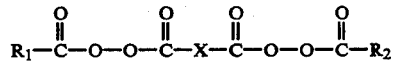

wherein X is an electron attracting substituted or unsubstituted phenylene group or a heterocycle in which the heteroatom is positioned so that from 2 to 4 carbon atoms are present between said heteroatom and each one of the two carbonyl carbons of the diperacid, or X is an electron attracting functional group positioned so that a carbon chain having from 2 to 4 carbon atoms is present between said electron attracting group and each one of the carbonyl carbons of the diperacid, wherein the electron attracting functional group contains oxygen, sulfur, nitrogen, phosphorus, halogen, substituted or unsubstituted phenyl or at least two conjugated double bonds, and $R_1$ and $R_2$ are hydrocarbon groups having from 1 to 15 carbon atoms.

2. A composition as claimed in claim 1, wherein X is phenylene or a substituted phenylene group, or an electron attracting functional group selected from sulfo, sulfonyl, thio, nitro, hydroxy, quaternary amine, amine oxide, carboxylic acid, ketone, aldehyde, ester or ether.

3. A composition as claimed in claim 2, wherein X is phenylene, nitrophenylene, hydroxyphenylene, aminophenylene, sulfophenylene, phenylcarboxylic acid, phenyldicarboxylic acid, or an electron attracting functional group selected from sulfonyl, amine oxide or quaternary amine.

4. A composition as claimed in claim 1, wherein $R_1$ and $R_2$ are alkyl groups having 1 or 2 carbon atoms.

5. A composition as claimed in claim 1, including a detergent builder.

6. A composition as claimed in claim 1, including a hydrogen peroxide generating substance.

7. A composition as claimed in claim 1, including at least one surfactant.

8. A composition as claimed in claim 1, including an alkali generating agent.

9. A method of bleaching in an alkaline environment, comprising the step of bringing the material to be bleached in contact with an alkaline aqueous solution containing a diacylated dipercarboxylic acid according to the formula:

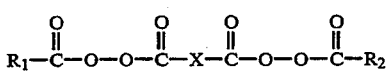

wherein X is an electron attracting substituted or unsubstituted phenylene group, a heterocycle in which the heteroatom is positioned so that from 2 to 4 carbon atoms are present between said heteroatom and the carbonyl carbons of the diperacid, or X is an electron attracting functional group positioned so that a carbon chain having from 2 to 4 carbon atoms is present between said electron attracting group and each one of the carbonyl carbons of the diperacid, wherein the electron attracting functional group contains oxygen, sulfur, nitrogen, phosphorus, halogen, substituted or unsubstituted phenyl or at least two conjugated double bonds, and $R_1$ and $R_2$ are hydrocarbon groups having from 1 to 15 carbon atoms.

* * * * *